US008784390B2

(12) United States Patent
Thomason et al.

(10) Patent No.: US 8,784,390 B2
(45) Date of Patent: Jul. 22, 2014

(54) SKIN TREATMENT SPRAY NOZZLE SYSTEM FOR AUTOMATIC SPRAY GANTRY

(75) Inventors: Scott Thomason, Macedonia, OH (US); Steven C. Cooper, Athens, GA (US)

(73) Assignee: Sunless, Inc., Macedonia, OH (US)

( * ) Notice: Subject to any disclaimer, the term of this patent is extended or adjusted under 35 U.S.C. 154(b) by 54 days.

(21) Appl. No.: 12/910,282

(22) Filed: Oct. 22, 2010

(65) Prior Publication Data
US 2011/0133004 A1    Jun. 9, 2011

Related U.S. Application Data

(60) Provisional application No. 61/266,810, filed on Dec. 4, 2009.

(51) Int. Cl.
*A61M 35/00* (2006.01)
(52) U.S. Cl.
USPC ............ 604/289; 604/290; 604/291; 239/10; 239/71; 239/135
(58) Field of Classification Search
CPC ............ A45D 2200/057; A61M 35/00; B05B 7/0815; B05B 7/1209; B05B 7/0081; B05B 7/32; B05B 7/066; B05B 7/0838; B05B 15/12; B05B 15/1248; B05B 15/1262; B05B 15/10; B05B 5/03; B05B 1/005; A61Q 19/04; A61K 2800/83
USPC ............ 604/289, 290, 291; 239/10, 71, 135, 239/207, 525, 526, 302
See application file for complete search history.

(56) References Cited

U.S. PATENT DOCUMENTS 1,586,009 A    5/1926    Shelburne
1,982,509 A    11/1934   Frank
(Continued)

FOREIGN PATENT DOCUMENTS

DE    3540990 A1    5/1987
DE    3720938 A1    1/1989
(Continued)

OTHER PUBLICATIONS

International Search Report and Written Opinion, mailed Feb. 3, 2011, for PCT/US/2010/058972 (16 pages).
(Continued)

*Primary Examiner* — Philip R Wiest
*Assistant Examiner* — Ariana Zimbouski
(74) *Attorney, Agent, or Firm* — Venable LLP; Steven J. Schwarz

(57) ABSTRACT

A spray nozzle system for skin treatments includes separate air outlets moving over the skin surface to deliver one or more streams of supplemental air for the purpose of warming or drying the skin surface to improve efficacy and comfort of the spraying experience. The drying air from the auxiliary ports may be applied while spray is emitted from the nozzle to increase the spray cloud temperature, or may be applied before or after the spray application, with the spray turned off, to warm or dry the skin. A heating source is provided to warm the air directed through one or more heated air ports. In the case of air-atomizing nozzles, the heated air is delivered through low pressure ports separately from the air emitted through the nozzle's higher pressure atomizing and pattern shaping orifices to minimize the expansion cooling effect inherent with the spray nozzle ports. In another implementation, the airflow is redirected from the nozzle jets to one or more of the supplemental ports using a control valve which proportions the amount of airflow directed to the main atomizer air jets, the pattern shaping air jets and the supplemental air for drying the skin.

42 Claims, 8 Drawing Sheets

(56) References Cited

U.S. PATENT DOCUMENTS

| | | |
|---|---|---|
| 2,139,133 A | 12/1938 | Paasche |
| 2,267,264 A | 12/1941 | Bland |
| 2,284,235 A | 5/1942 | Ronzi |
| 2,401,504 A * | 6/1946 | Paasche ............ 239/133 |
| 3,007,178 A | 11/1961 | Altman et al. |
| 3,057,558 A | 10/1962 | Verba et al. |
| 3,344,992 A | 10/1967 | Norris |
| 3,437,791 A | 4/1969 | Gardner |
| 3,587,118 A | 6/1971 | Compton |
| 3,596,834 A * | 8/1971 | Cushing ............ 239/255 |
| 3,662,407 A | 5/1972 | Colucci |
| 3,721,250 A | 3/1973 | Walter et al. |
| 3,759,449 A * | 9/1973 | Ruthman et al. ........ 239/416.2 |
| 3,770,201 A | 11/1973 | Sanders |
| 3,780,943 A | 12/1973 | Lilja |
| 3,854,489 A | 12/1974 | Doyle et al. |
| 3,905,379 A | 9/1975 | Churas et al. |
| 3,947,659 A | 3/1976 | Ono |
| 3,989,143 A | 11/1976 | Broussard |
| 4,056,078 A | 11/1977 | Blafford et al. |
| 4,114,022 A | 9/1978 | Braulke, III |
| 4,130,120 A | 12/1978 | Kohler, Jr. |
| 4,149,536 A | 4/1979 | Villard |
| 4,166,473 A | 9/1979 | Bauer et al. |
| 4,300,556 A | 11/1981 | Ochi et al. |
| 4,382,424 A | 5/1983 | Altissimo |
| 4,386,739 A | 6/1983 | Kwok |
| 4,394,967 A | 7/1983 | Amiaut |
| 4,485,503 A | 12/1984 | Rolando et al. |
| 4,505,229 A | 3/1985 | Altissimo |
| 4,523,080 A | 6/1985 | Bolton |
| 4,597,757 A | 7/1986 | Ruderian |
| 4,605,019 A | 8/1986 | Reynolds et al. |
| 4,761,837 A | 8/1988 | Takeda |
| 4,836,137 A | 6/1989 | Heine et al. |
| 4,901,379 A * | 2/1990 | Chalberg et al. .......... 4/541.5 |
| 4,915,303 A | 4/1990 | Hufgard |
| 5,038,769 A | 8/1991 | Krauser |
| 5,074,322 A | 12/1991 | Jaw |
| 5,078,322 A | 1/1992 | Torntore |
| 5,102,051 A | 4/1992 | Smith et al. |
| 5,136,735 A | 8/1992 | Zimmerman |
| 5,199,644 A * | 4/1993 | Haferkorn ............ 239/296 |
| 5,228,150 A | 7/1993 | Parker |
| 5,241,974 A | 9/1993 | Tsai |
| 5,261,427 A | 11/1993 | Dolev |
| 5,339,540 A | 8/1994 | Edwards |
| 5,387,200 A | 2/1995 | Kronstadt |
| 5,520,519 A | 5/1996 | Birkeland |
| 5,558,276 A | 9/1996 | Barrett et al. |
| 5,603,341 A | 2/1997 | Johnson |
| 5,642,570 A | 7/1997 | Lee |
| 5,664,593 A | 9/1997 | McClain |
| 5,864,894 A | 2/1999 | Fedele |
| 5,971,298 A | 10/1999 | Millan et al. |
| 5,991,937 A | 11/1999 | Safara |
| 6,106,547 A | 8/2000 | Huei-Jung |
| 6,117,915 A | 9/2000 | Pereira et al. |
| 6,302,122 B1 | 10/2001 | Parker et al. |
| 6,387,081 B1 | 5/2002 | Cooper |
| 6,416,747 B1 | 7/2002 | Laughlin |
| 6,418,573 B1 | 7/2002 | Masuda |
| 6,554,208 B1 | 4/2003 | Venuto, Sr. |
| 6,673,097 B1 | 1/2004 | Venuto, Sr. |
| 6,802,830 B1 | 10/2004 | Waters et al. |
| 6,923,794 B2 | 8/2005 | Ohmura |
| 6,973,679 B1 | 12/2005 | Schad |
| 7,041,089 B2 * | 5/2006 | Laughlin ............ 604/289 |
| 7,132,010 B2 | 11/2006 | Carlsson |
| 7,297,211 B2 | 11/2007 | Cooper et al. |
| 7,387,684 B2 | 6/2008 | Cooper et al. |
| 7,462,242 B2 | 12/2008 | Cooper et al. |
| 7,569,037 B1 | 8/2009 | Spivak |
| 7,772,526 B2 | 8/2010 | Chuong |
| 2002/0000237 A1 | 1/2002 | Laughlin |
| 2003/0029488 A1 | 2/2003 | Baird |
| 2003/0094510 A1 | 5/2003 | Laughlin |
| 2004/0147884 A1 | 7/2004 | Szurko |
| 2004/0156793 A1 | 8/2004 | Golden et al. |
| 2004/0228810 A1 | 11/2004 | Hamson et al. |
| 2005/0059910 A1 | 3/2005 | Licht et al. |
| 2005/0150467 A1 | 7/2005 | Segura Jobal |
| 2005/0242207 A1 | 11/2005 | Tejeda |
| 2005/0279865 A1 | 12/2005 | Thomason et al. |
| 2005/0281957 A1 * | 12/2005 | Cooper et al. ............ 427/458 |
| 2006/0032946 A1 | 2/2006 | Cooper et al. |
| 2006/0064815 A1 | 3/2006 | Guerin et al. |
| 2006/0102096 A1 | 5/2006 | Cho |
| 2006/0118039 A1 | 6/2006 | Cooper |
| 2006/0163382 A1 | 7/2006 | Spivak et al. |
| 2006/0207013 A1 | 9/2006 | Deboer et al. |
| 2006/0214027 A1 | 9/2006 | Micheli |
| 2006/0231567 A1 | 10/2006 | Perrone |
| 2006/0275555 A1 | 12/2006 | Colizza et al. |
| 2006/0278661 A1 | 12/2006 | Cooper et al. |
| 2007/0107121 A1 | 5/2007 | Smith et al. |
| 2007/0169261 A1 * | 7/2007 | Smith et al. ............ 4/615 |
| 2007/0197982 A1 * | 8/2007 | Thomason et al. ........ 604/289 |
| 2007/0275021 A1 | 11/2007 | Lee et al. |
| 2008/0071332 A1 | 3/2008 | Nelson et al. |
| 2008/0237522 A1 * | 10/2008 | Morris ............ 251/315.01 |
| 2009/0114236 A1 | 5/2009 | Mehta |
| 2009/0130044 A1 | 5/2009 | Choi et al. |
| 2009/0272316 A1 | 11/2009 | Arnaud et al. |
| 2009/0314857 A1 | 12/2009 | Thomason et al. |
| 2010/0065655 A1 | 3/2010 | Hipperson |
| 2010/0266776 A1 | 10/2010 | Cooper et al. |
| 2011/0060195 A1 | 3/2011 | De Noray et al. |
| 2011/0133001 A1 | 6/2011 | Cooper et al. |
| 2011/0137268 A1 | 6/2011 | Thomason et al. |
| 2011/0202019 A1 | 8/2011 | Cooper et al. |
| 2011/0259974 A1 | 10/2011 | Cooper et al. |
| 2012/0056017 A1 | 3/2012 | Thomason et al. |
| 2013/0020414 A1 | 1/2013 | Thomason et al. |
| 2013/0262033 A1 | 10/2013 | Henson |

FOREIGN PATENT DOCUMENTS

| | | |
|---|---|---|
| EP | 0359943 A2 | 3/1990 |
| GB | 2139885 A | 11/1984 |
| GB | 2432785 A | 6/2007 |
| JP | 2000135111 A | 5/2000 |
| WO | WO-2004033107 A2 | 4/2004 |
| WO | WO-2004069322 A1 | 8/2004 |
| WO | WO-2004084983 A1 | 10/2004 |
| WO | WO-2010012903 A1 | 2/2010 |
| WO | WO-2010123922 A1 | 10/2010 |

OTHER PUBLICATIONS

EPO Supplemental Search Report for EP 10835224 mailed May 15, 2013 (7 pages).

Tanning Essentials, Manual: Classic Tanning Essentials Spray Tan System, date unknown (8 pages).

Croda Material Safety Data Sheet, Croda Document #Croda-Pro; SHE-51, Attachment A, Revision Date Dec. 9, 2005 (4 pages).

Crodafos CES Product Brochure, Croda Inc., Feb. 9, 2010 (9 pages).

Crodafos(tm) CES Data Sheet, "Targeted Delivery Agent for Skin Care," INCI Name: Cetearyl Alcohol (and) Dicetyl Phosphate (and) Ceteth-10 Phosphate, PN-094R-1, Jan. 28, 2009 (10 pages).

Crodafos(tm) CS20A Data Sheet, Cetearyl Alcohol (and) Ceteth-20 Phosphate, "Primary Emulsifier for Pourable or Sprayable Emulsions," Apr. 14, 2010, DS-156R-7 (9 pages).

VersaSpa(tm) age-defying sunless tanning and More: "HVLP Automatic Skin Treatment System, Owner's Manual Version 5.0," Sep. 2006 (42 pages).

* cited by examiner

SKIN TREATMENT SPRAY NOZZLE SYSTEM FOR AUTOMATIC SPRAY GANTRY

PRIORITY CLAIM

This application claims priority from U.S. Provisional Application for Patent No. 61/266,810, filed Dec. 4, 2009, the disclosure of which is hereby incorporated by reference.

BACKGROUND

Spray devices for the application of liquids onto human skin and hair are well known. Sprays are used for many types of medicines, skin treatments, hair treatments, deodorants, lotions, and cosmetic agents. Specialized hand-held and automated spray systems have recently been introduced in tanning salons and spa treatment centers to apply sunless tanning compounds and skin care formulas, such as moisturizers, anti-aging treatments, and exfoliants. The spray solution used for sunless tanning is generally a water-based mixture of DHA (dihydroxyacetone) and/or erythrulose and various other skin care ingredients such as aloe vera. Often a cosmetic bronzer is added along with pleasant scents and ingredients to enhance tanning performance, such as formulations to balance skin ph.

The skin treatment spray process has inherently been a cold, uncomfortable experience for the recipient as nozzle expansion significantly cools the air and liquid in the spray cloud during application to the skin. Furthermore, cold skin is known to inhibit optimum absorption of the skin care ingredients. Temperatures of the spray cloud can be over 30 degrees (F.) lower than human body temperature due to nozzle cooling. Heating of the spray liquid or the atomization air has a negligible effect on increasing spray cloud temperature due to the rapid cooling produced as the spray jet expands when exiting the nozzle. This phenomenon is magnified when using air-atomizing nozzles; the type most desirable for producing a finely atomized spray.

In salons, customers disrobe for the spray treatment which lasts from 30 seconds to 5 minutes. Some treatments involve sequential spray regimens of alternate ingredients so the experience can be significantly longer. Thus, the length of time the customer is exposed to cold can be significant and may discourage the customer from obtaining the treatment in the first place or returning for additional treatments at later dates.

After the spray treatment customers often use a towel to dry their skin. The action of toweling-off removes a significant quantity of the sprayed ingredients from the skin. The remaining ingredients may be redistributed, which can produce a splotchy appearance in the case of sunless tanning or other cosmetic treatments. If the customer opts not to use a towel, and instead simply dry off in the ambient air or from the cool air of air-atomizing nozzles, the surface of the skin can become sticky.

Many tanning salons providing the new sunless spray tanning service also have conventional UV lamp tanning beds. Customers have observed that using the automated sunless tanning spray booths quickly after they use a UV tanning bed can result in a deeper and darker DHA tan. It is important to move from the UV tanning bed to the spray booth as quickly as possible. It is also essential to remove all perspiration resulting from the UV treatment or the tan result can be uneven. The benefits of UV tanning coupled with a sunless tanning spray may be due to opening the pores of the skin and from more thoroughly and more deeply drying out of the top skin layer by the hot UV lamps. However, due to skin health concerns, many customers do not wish to use the UV beds and therefore cannot take advantage of this practice to enhance their sunless tan.

DHA tans the skin by reacting with proteins in the stratum corneum, the top protective skin layer composed of dead skin cells. It is known that only the uppermost dry layers of the stratum corneum will tan effectively with DHA or erythrulose. Very dry skin will pigment the darkest and layers containing moisture will not tan nearly as well. Skin care specialists suggest using a warm towel on the skin before application of spray treatments since warm skin may better absorb some ingredients. However, a skin surface that is too hot will perspire, thus reducing the effectiveness of the sprayed ingredients.

A need exists in the art to address the foregoing issues in connection with providing a better sunless tanning experience and result for the consumer.

Reference is further made to Venuto, U.S. Pat. No. 6,554,208 (the disclosure of which is hereby incorporated by reference) which teaches a tanning spray booth implementation operable to both spray tanning solution and deliver drying air when not spraying.

Reference is also made to Safara, U.S. Pat. No. 5,991,937 (the disclosure of which is hereby incorporated by reference) which teaches a bidet sprayer implementation operable to both spray cleaning water and deliver drying air when not spraying.

SUMMARY

Embodiments disclosed herein propose the controlled application of warm dry air over the skin before, during and after applications of sunless tanning sprays in an automated gantry application. This controlled application enhances efficacy of the tanning compounds and results in a deeper tan color and a longer lasting tan. In addition, the mixing of heated dry air into the spray cloud reduces the discomfort caused by the inherently cold spray stream. Furthermore, warm dry air, applied during and after short spray sequences enhances the spray uniformity result and produces a softer characteristic feel of the spray ingredients on the skin, while reducing complaints of "stickiness" or "tackiness" by the consumer. Deposition efficiency and uniformity of the tan result is improved since the towel dry step after the spray session is no longer necessary.

A spray nozzle system is presented for applying topical skin treatments, such as sunless tanning formulations, medicines, and lotions. Specifically, liquids or suspensions are applied to human skin in an automated treatment spray booth where a microcontroller sequences operation of moving spray nozzles, a heated air system and liquid dispensing systems.

A spray nozzle system includes auxiliary air outlets positioned near the liquid spray outlet to deliver one or more streams of heated air (supplementing air supplied for atomization and pattern shaping) for the purpose of drying the skin surface and improving the comfort of the spraying experience. The drying air from the auxiliary ports may be applied while spray is emitted from the nozzle to increase the spray cloud temperature, or may be applied before or after the spray application, with the spray turned off, to warm or dry the skin.

A heating source is provided to heat air that is directed through one or more heated air outlets. In a preferred embodiment, a heating element is incorporated into the system. The heating element may be positioned at the air outlet or in the air hose to the air outlets or at the air pump. In the case of air atomizing nozzles, the heated air is delivered through low pressure outlets separate from (i.e., supplemental to) the air emitted through the nozzle's higher pressure atomizing and pattern shaping orifices to minimize the expansion cooling effect inherent with the spray nozzle ports. The heated air may be delivered through low pressure ports which move with the spray nozzle, are stationary with respect to the spay nozzle, or move independently of spray nozzle movement.

In another embodiment, the heated airflow is redirected from use at the nozzle jets (for atomization and/or pattern shaping) to one or more of the low pressure heated air outlets. In this embodiment, a control valve may be used to proportion the amount of airflow directed to the main high pressure atomizer air jets, the high pressure pattern shaping air jets and the low pressure air outlets for drying the skin.

The method of applying warm dry air between layered applications of spray has been found to make the experience of skin spray treatments much more comfortable as well as improve coating uniformity. In addition, this method provides an improved tack-free feel of the spray deposit on the skin both during and after the spray session. In the case of sunless tanning with active ingredients such as Erythrulose or DHA (dihydroxyacetone), the system provides for an improved tanning color and increased longevity of the tan.

In an embodiment, a system comprises: a gantry including a movable mount; a spray nozzle mounted to the movable mount for movement in at least one direction, the spray nozzle including a spray jet outlet adapted to spray a skin treatment liquid from the spray nozzle in a spray stream, the spray nozzle further including an air outlet adapted to deliver air from the spray nozzle in an air stream separate from the spray stream; a heating unit adapted to heat and deliver the air to the spray nozzle for the air stream; and a control system adapted to control movement of the spray nozzle along the movable track and operation of the spray nozzle.

In another embodiment, a system comprises: a support structure; a spray nozzle mounted to the support structure, the spray nozzle including a spray jet outlet adapted to spray a skin treatment liquid from the spray nozzle in a spray stream, the spray nozzle further adapted to provide for movement of the spray nozzle and direction of the spray stream; an air outlet mounted to the support structure, the air outlet adapted to deliver air in an air stream separate from the spray stream, the air outlet further adapted to provide for movement of the air outlet and direction of the air stream in a manner generally corresponding to the direction of the spray stream; a heating unit adapted to heat and deliver the air to the air outlet for the air stream; and a control system adapted to control operation of the spray nozzle spray jet outlet and air outlet as well as movement of the directions of the air stream and spray stream.

In another embodiment, a spray system comprises: a spray nozzle adapted to spray liquid on a skin surface; one or more auxiliary air outlets positioned near a liquid spray outlet of the spray nozzle which are adapted to deliver one or more streams of supplemental warming air; and a controller operable in a first mode to cause delivery of the one or more streams of supplemental warming air from the one or more auxiliary air outlets simultaneously with delivery of the spray liquid from the spray nozzle for the purpose of warming the spray liquid, and further operable in a second mode to cause delivery of the one or more streams of supplemental warming air from the one or more auxiliary air outlets alternately with delivery of the spray liquid from the spray nozzle for the purpose of drying a target surface.

BRIEF DESCRIPTION OF THE DRAWINGS

A more complete understanding of the invention may be obtained by reference to the following drawings.

DETAILED DESCRIPTION OF THE DRAWINGS

Figure 1A:
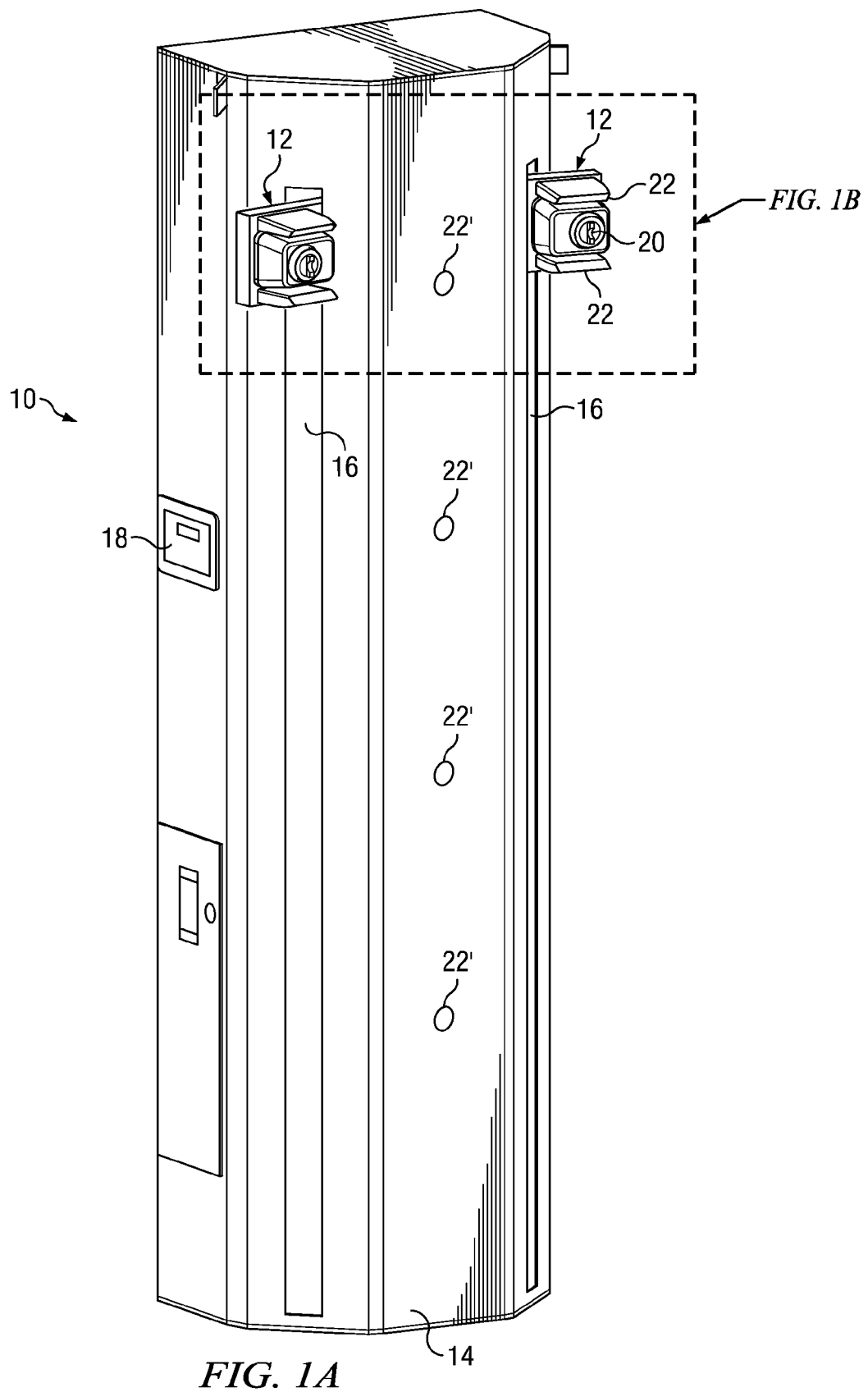
FIGS. 1A and 1B illustrate an automatic system for spraying skin treatment solutions.
Figure 1B:
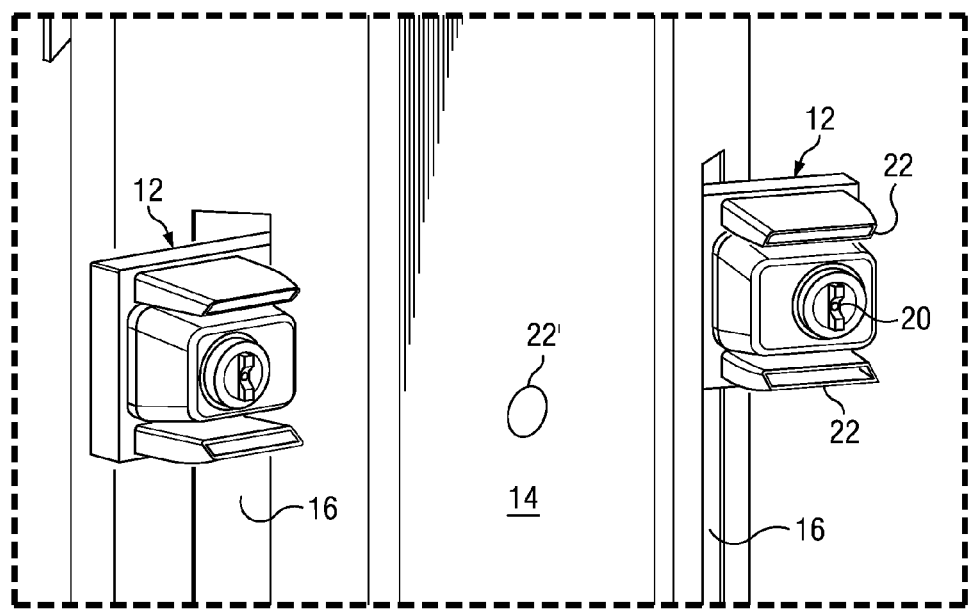

FIGS. 1A and 1B illustrate an automatic system 10 for spraying skin treatment solutions. The system 10 comprises one or more spray nozzles 12 installed on a gantry 14 that is configured to move the nozzle in at least one direction. In a preferred implementation, the gantry 14 is configured with a mechanism to traverse each nozzle along a linear guide track 16 having a vertical orientation. In another implementation, the nozzle 12 is installed on a gantry including a multi-axis robotic guide mechanism configured to move the nozzle in at least one linear direction (for example, vertical) and may further support movement in another linear direction (such as, for example, horizontal). In another implementation, the nozzle 12 is installed on gantry including a pivot mechanism to support change in the angular orientation of the spray direction (for example, vertical and/or horizontal). Combinations of the foregoing movement mechanisms may be employed by the gantry if desired. A control panel 18 is coupled to a control system (see, FIG. 3) which controls gantry operation to move the nozzle 12 (for example, along the linear guide track 16, or in any supported linear direction or angular orientation). Each nozzle 12 is mounted to the gantry and includes a spray outlet 20 (or multiple spray outlets 20) and a low pressure air outlet 22 (or multiple low pressure air outlets 22). The control system further controls actuation of each nozzle 12 to output from the one or more spray outlets 20 a spray jet containing a skin treatment solution. The control system further controls actuation of each nozzle 12 to output from the one or more air outlets 22 a stream of heated air flow (which is supplemental to any high pressure air used at the spray outlets 20 for atomization and/or pattern shaping). The air outlets 22 for providing heated air are positioned both above and below the spray outlet 20 on each nozzle 12, although it will be understood that only a single outlet 22 (adjacent the spray outlet 20) is necessary. A heating element (reference 58, FIG. 3) is provided to heat the air delivered to and output from the heated air outlet 22.

In a preferred embodiment the spray jet from spray jet outlet 20 of the nozzle 12 is controlled separately from the air flow from heated air outlet 22 to allow a sequence of operations to be performed in connection with the spraying skin treatment, such as pre-warming of the skin, followed by separate spraying and drying cycles. The heated air flow from the air outlets 22 positioned above and below the spray outlet 20 is provided in a controlled manner for a number of purposes:

to pre-warm the skin, to warm both the leading and trailing edges of the spray jet (i.e., the spray cloud) as the jet is naturally bent due to movement of the nozzle 12 along the guide track 16, and to provide a drying air stream after the spray cloud passes (or independent of spray cloud application).

In operation, the system 10 is controlled to move among and between various operating modes as described herein. The control system controls delivery of liquid spray from the nozzle spray jet outlet 20 and/or the delivery of heated air from the air outlet 22 before, during or after the liquid spray is applied. In essence, the control system functions to control the application of the liquid spray and low pressure heated air (for example, simultaneously or sequentially/alternatively). Additionally, the heating element may be controlled by the control system 18 to adjust an amount of heat provided and thus control the temperature of the heated air flow delivered from the air outlet 22. The control system further controls a valve (reference 60, FIG. 3) for passing the liquid skin products from a tank to the nozzle for delivery in the liquid spray from the spray jet outlet 20.

The movement among and between modes is designed to enhance the consumer's spray tanning experience and improve the tanning result. Warm air from the air drying outlet serves to prepare the skin for treatment, warm the skin for customer comfort, and dry the skin evenly after application. Alternating between spray application and warm air application improves the tanning result. Furthermore, the mixing relatively low pressure warm air application in with liquid spraying (i.e., mixing into the spray cloud) reduces the discomfort experienced by the consumer due temperature drop of the spray liquid resulting from high pressure nozzle expansion effects.

It will further be recognized that the heated air could be supplied from low pressure air outlets 22' positioned on the gantry tower separate from the spray nozzles 12. Furthermore, these air outlets 22' could themselves be selectively movable (for example, on a separate track system, robotic control system, pivoting mechanism, or through oscillation of direction of application) under the control of the control system in order to better circulate the heated air or better direct and move the air across the customer's body.

Figure 2:
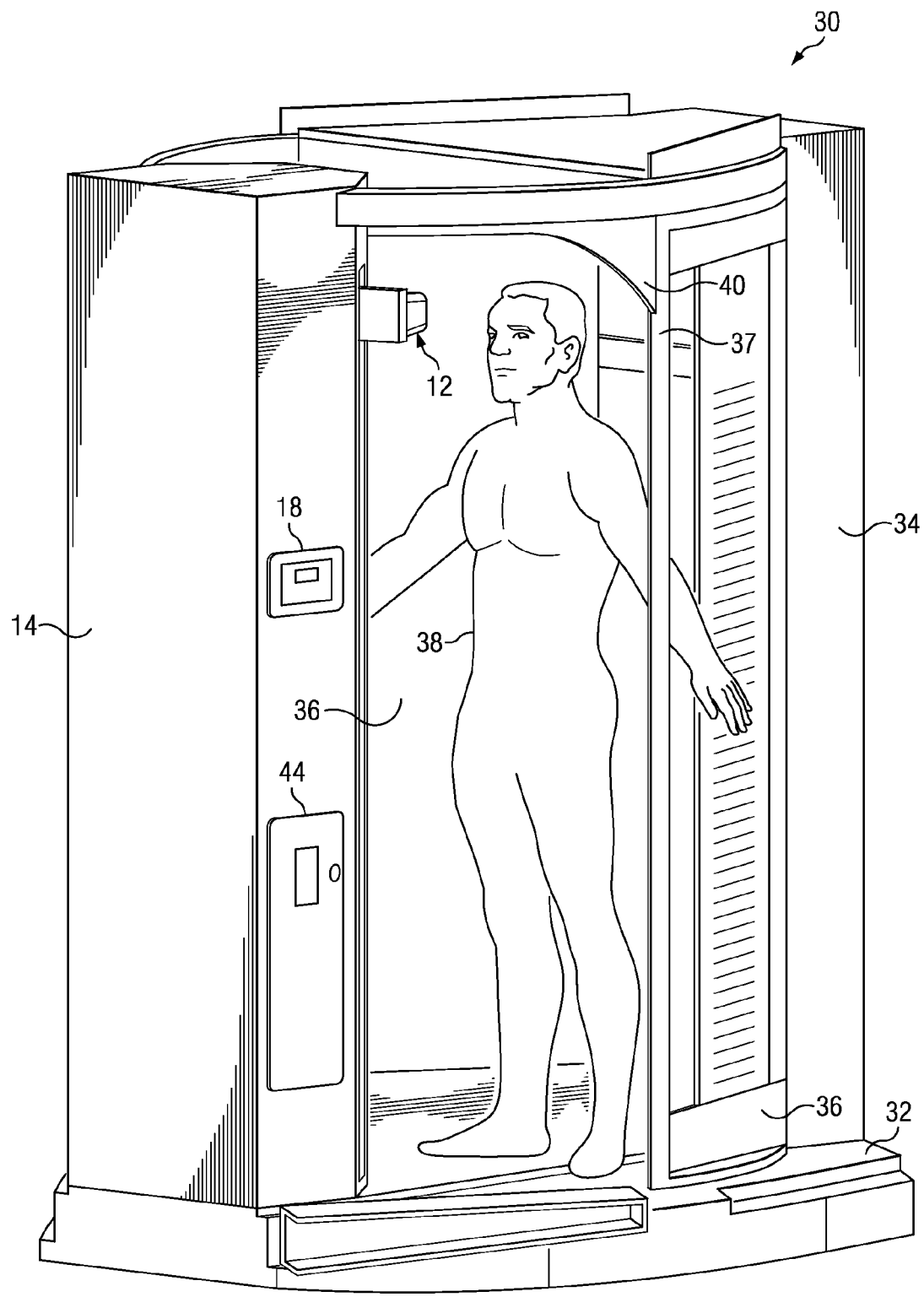
FIG. 2 illustrates installation of the spraying system of FIGS. 1A and 1B within an enclosure.

Reference is now made to FIG. 2 which illustrates installation of the spray system of FIGS. 1A and 1B within an enclosure such as a spray booth 30. As discussed above, the spray nozzles 12 on the gantry 14 not only provide for the delivery of spray liquid but further function to deliver heated air for the purposes of: warming the spray cloud during liquid spraying; warming the spray booth (area) before and after spraying; and drying the target between and after liquid spray applications. As noted, the booth 30 may provide either a partial enclosure or a full enclosure during the spray application (and furthermore no booth at all is needed in some implementations). The booth 30 is further configured with multiple solution storage containers (i.e., multiple tanks each containing solution to be sprayed) to support the application of different types of spray liquids in accordance with customer requests. The nozzle 12 may further be configured to accept in a receptacle a single dose container of solution (or a small container).

The booth 30 includes a base 32 supporting, at one end thereof, the gantry 14 (as shown in FIGS. 1A and 1B). The base 32 further supports, at an opposite end thereof, an exhaust system 34 which functions to clear fumes, overspray, vapor, etc. from, the booth 30 as well as encourage the circulation of air within the booth (both before, during and after a spray session). The booth 30 further includes side walls 36 to provide an enclosure. It will be understood that the enclosure need not be complete, and it will further be understood that in some implementations no booth is necessary. Furthermore, one of the side walls 36 contains an opening 37 to allow entrance to and exit from the booth 30 by the customer 38, and that the opening can further support a door to provide for a completely enclosed booth. An overspray and heat containment baffle 40 is provided in an upper corner of the opening in the side wall 36. A customer interface control panel 18 is provided on the exterior of the gantry 14 (although it will be understood that the control 18 may be provided remote from the spray system in some installations). It is through this interface that the customer 38 can make selections and control operation of the spraying system (via the control system). An access door 44 is provided on the exterior of the gantry 14. It is through this access door 44 that service, repairs and refilling of the spraying system can be made.

Examples of booth 30 implementations for spraying human targets are well known to those skilled in the art.

Figure 3:
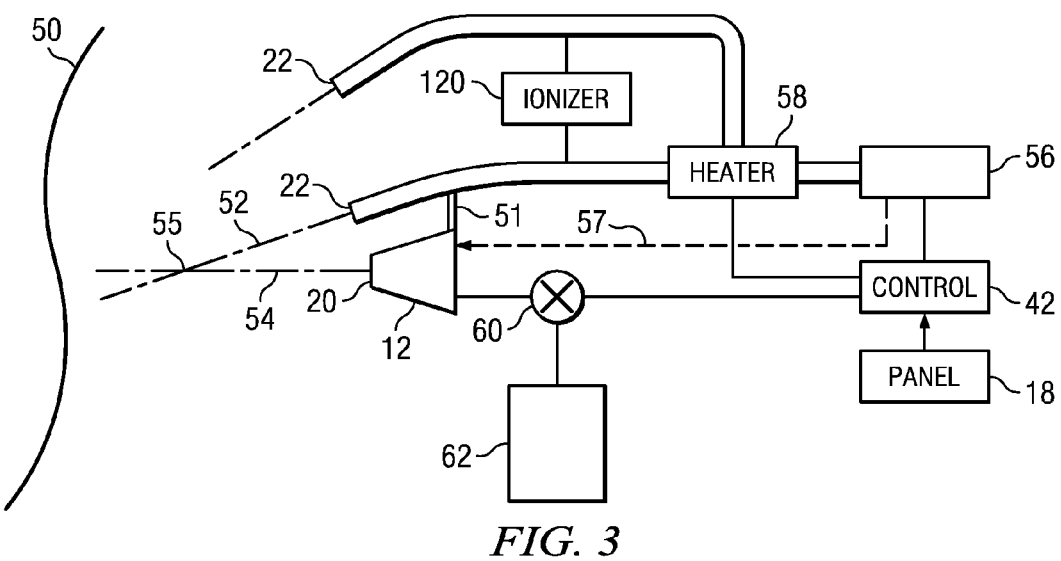
FIG. 3 schematically illustrates a spraying system adapted for use, for example, in the implementation of FIGS. 1A and 1B.

Reference is now made to FIG. 3 which schematically illustrates a spraying system adapted for use, for example, in the implementation of FIGS. 1A and 1B. The system is configured to separately apply spray and drying/warming air to the target surface 50 (for example, a customer's skin). The nozzle 12 includes a spray jet outlet 20 and a heated air outlet 22. These structures are preferably attached together (reference 51) and therefore will move together, such as along the guide track provided by the gantry 14 of FIGS. 1A and 1B, in the case of an automated spray booth (as shown in FIG. 2). It will, of course, be understood that the air outlet 22' could be separated from the moving spray jet outlet 20 on the nozzle 12 (as also shown in FIGS. 1A and 1B). Thus, a second device could be employed to move the heated air outlet 22' corresponding with respect to, or independently of, the nozzle spray jet outlet 20.

The low pressure heated air stream 52 and the spray nozzle jet stream 54 are both directed towards the target surface 50. In a preferred embodiment, the heated air stream 52 intersects 55 the spray steam 54 (or more particularly the cloud of spray fluid produced by the nozzle 12 spray jet outlet 20) so as to mix heated air into the spray cloud. Ambient air through a fan, blower or compressor 56 may be used as a source of the air stream 52. Additionally, as discussed above, a heating element 58 may be incorporated at a suitable place in the line of this air flow to receive the air from the fan, blower or compressor. The heating element 58 may be placed either at the air outlet 22/22' or positioned remotely there from. The air source (blower, etc. 56) for the air may be located at the nozzle 12 or positioned remotely there from. Additionally, if an air atomizer is used for the nozzle 12 it may be desired to use a common compressor (source 56) for sourcing air to the air atomizing nozzle 12 (for use in a high pressure configuration) and sourcing air to the supplemental air output 22 (as shown with dotted line 57 for use in a low pressure configuration), rather than have a separate source of air for each. The compressor of source 56 may be any air moving device suitable for operation, such as a fan, blower, turbine, or piston, rotary or diaphragm compressor, or other air pump. The system accordingly provides for one or more moving point sources of heated air to be mixed into the spray cloud. Advantages of this implementation (for example, in comparison to a large dispersed area heating source) include: reduced power requirements; localized delivery of heated air both to the spray cloud and towards the target; and the moving air provides a massaging effect on the target and dries the target skin more quickly and efficiently.

The control panel 18 is coupled to a control system 42 which controls actuation of the spray nozzle 12 for delivery of the spray nozzle jet stream 54 from outlet 20 as well as controls the application of the heated air stream 52 from outlet 22 before, during or after the spray is applied. The control system 42 may comprise, for example, a microcontroller and the control panel may comprise, for example, a touchscreen display. The control system 42 functions to control the application of spray and heated air in a number of operating modes including, for example, simultaneously application and/or sequential/alternative application. Additionally, if a heating element 58 is used, the control system 42 may also adjust the amount of heat (i.e., the temperature of the heated air stream 52). The control system 42 is further connected to the air source 56 to control the amount of air flow in the heated air stream 52 delivered from the air outlet 22. The control system 42 is further connected to a valve 60 which controls passing of liquid skin products from a tank 62 (or selects from more than one tank) to the nozzle 12 for spraying.

It will be understood that the spray nozzle 12 can comprise an electrostatic nozzle (inductive, ionizing or contact charged) as known to those skilled in the art.

Figure 4:
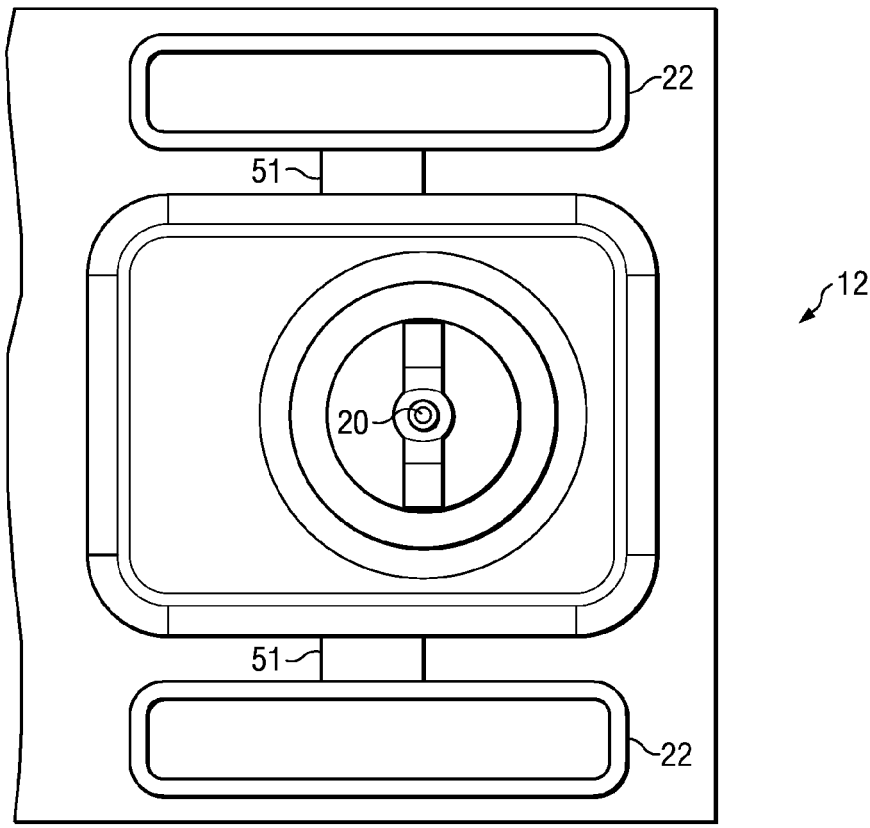
FIG. 4 illustrates a front view of an air atomizing spray nozzle for use in the spraying system of FIGS. 1A and 1B.

FIG. 4 shows the front view of an air atomizing spray nozzle 12 with heated air outlets 22 positioned around the nozzle spray outlet 20. Two air outlets 22 are shown (one above and one below the nozzle spray outlet 20). However, it will be understood that a single outlet 22 may be used, or that more than two outlets 22 could be used. The outlets 22 are coupled 51 to the nozzle outlet 20 so that the outlets may move together as a group, for example as the nozzle 12 is traversed by the gantry 14 in a least one direction (such as along the guide track as shown in FIGS. 1A and 1B). With such a moving nozzle 12 implementation, it is preferred that a heated air outlet 22 be located on at least the leading edge or edges of the predominant direction of nozzle motion (in the case, vertical). The outlet 22 is configured to deliver heated air in the heated air stream 52. In an embodiment, it is an advantage of the disclosed system that this heated air is delivered towards the customer and is felt on the customer's skin before the spray nozzle jet stream 54 (and its associated spray cloud) hits the customer's skin. In a preferred embodiment, heated air outlets 22 are positioned on both the leading and trailing edges so as to allow for an optimal mixing of heated air with the spray cloud (on the leading edge) and provide a drying effect after the spray passes over the skin (on the trailing edge).

Although an air atomizing nozzle is shown in FIG. 4, it will be understood that a suitable hydraulic nozzle, sonic or other type nozzle could alternatively be used. In the case of an air-atomizing nozzle, either a single air source or separate air sources may be used for the heated air (as supplemental air) and the atomizing and/or pattern shaping air used by the air-assisted nozzle. In the case of an air-assisted high volume, low pressure (HVLP) nozzle, the turbine itself can be used as a heated air source; conduits can be ported to provide air at a higher pressure for atomization and pattern shaping, and provide air at a lower pressure for drying and warming. Additionally, one or more heating elements can be incorporated directly into air conduits or at the exit of the drying air outlets.

Figure 5:
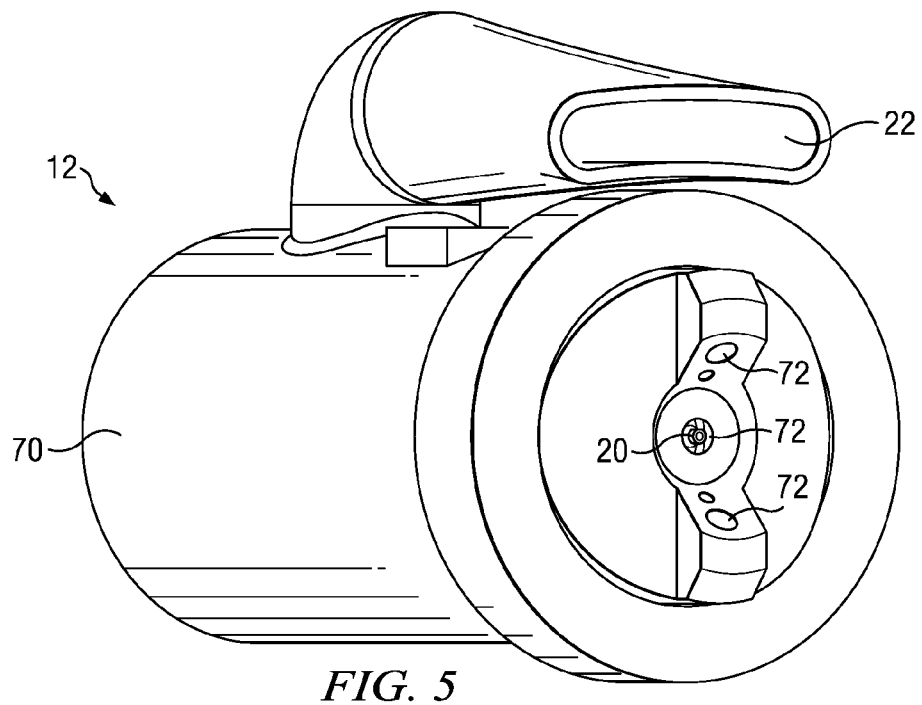
FIG. 5 illustrates a perspective view of an HVLP type of spray nozzle configured with an auxiliary air port for providing heated air.
Figure 6:
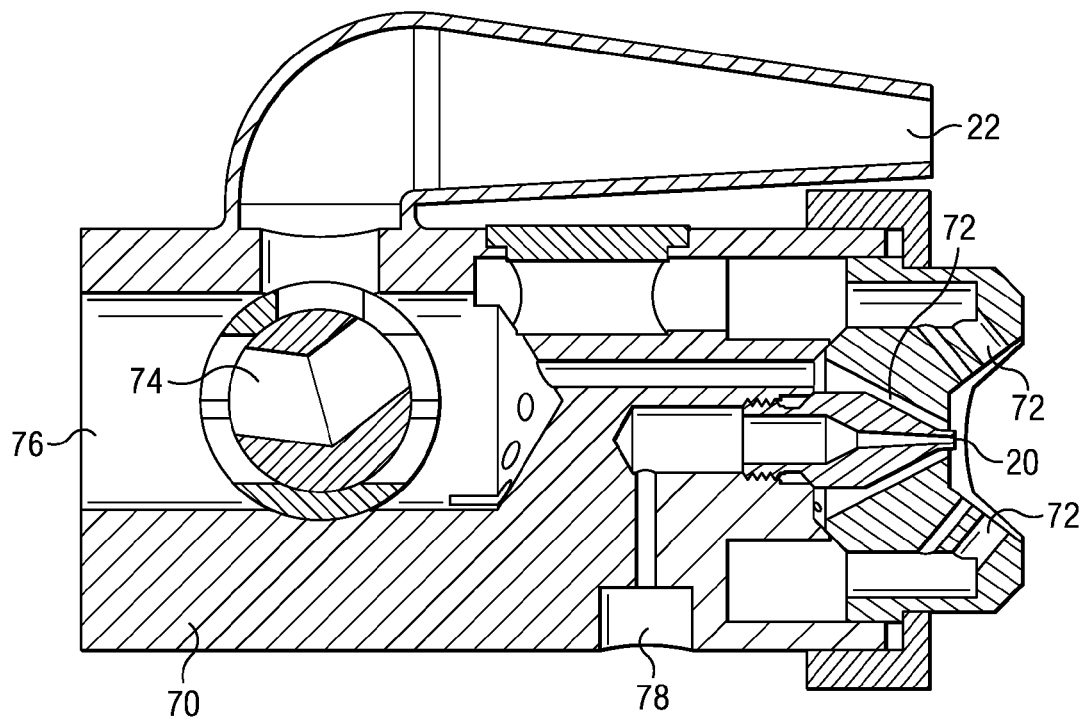
FIG. 6 is a cross-sectional view of the nozzle of FIG. 5.
Figure 7A:
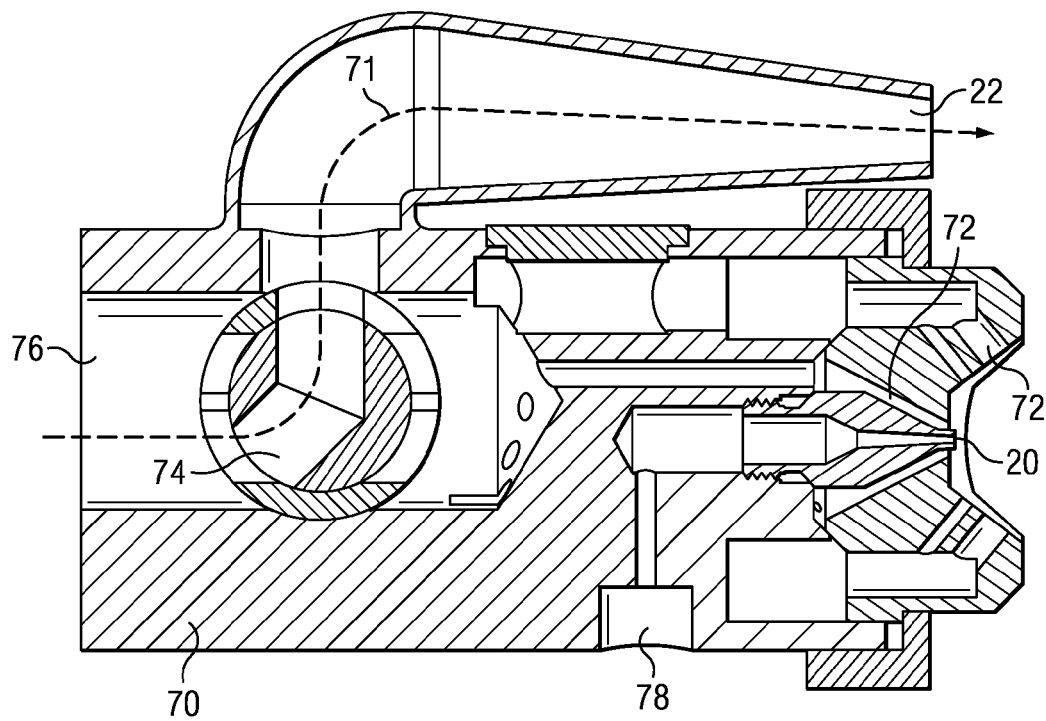
FIGS. 7A to 7C illustrate modes of operation for the nozzle of FIGS. 5 and 6.
Figure 7B:
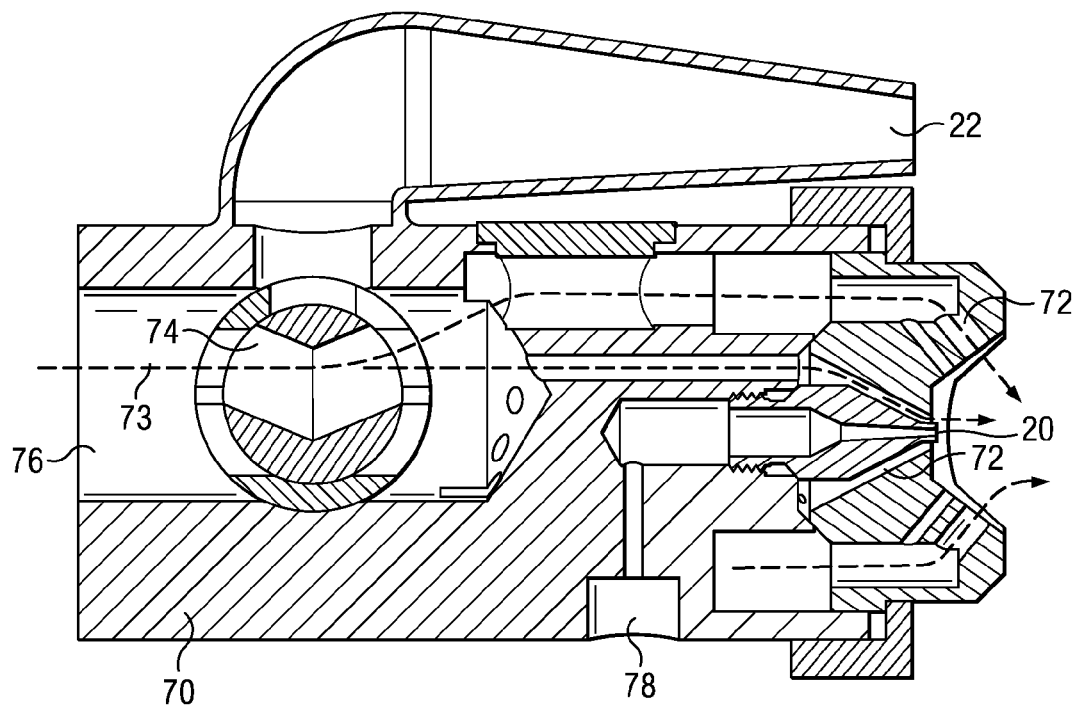
Figure 7C:
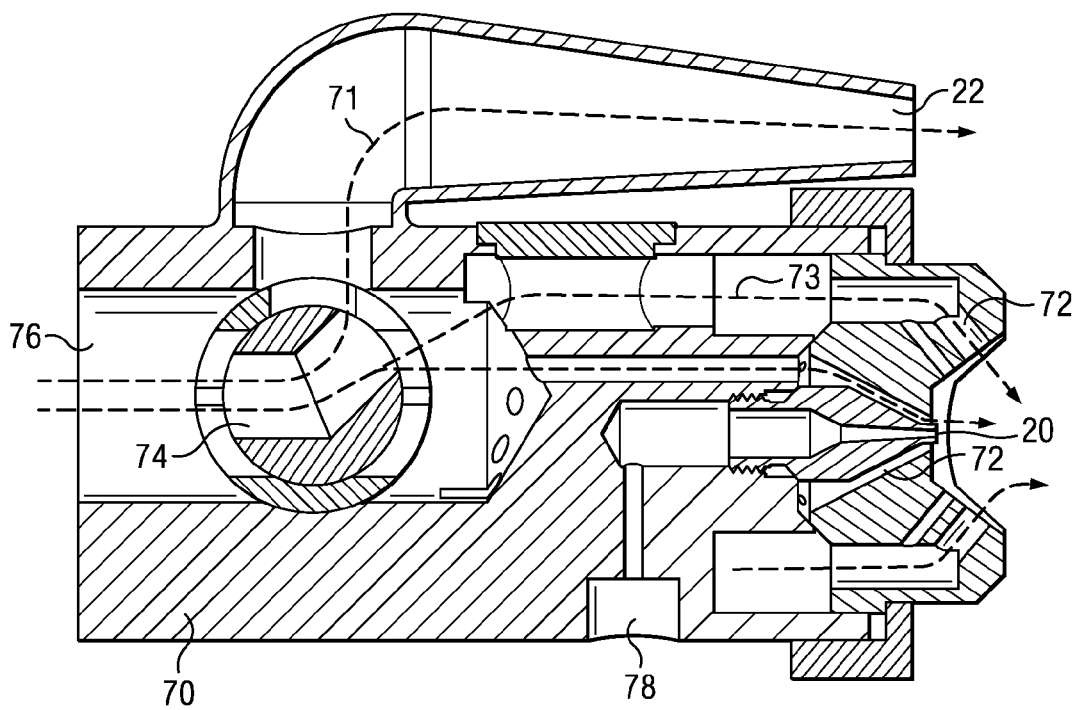
Figure 9:
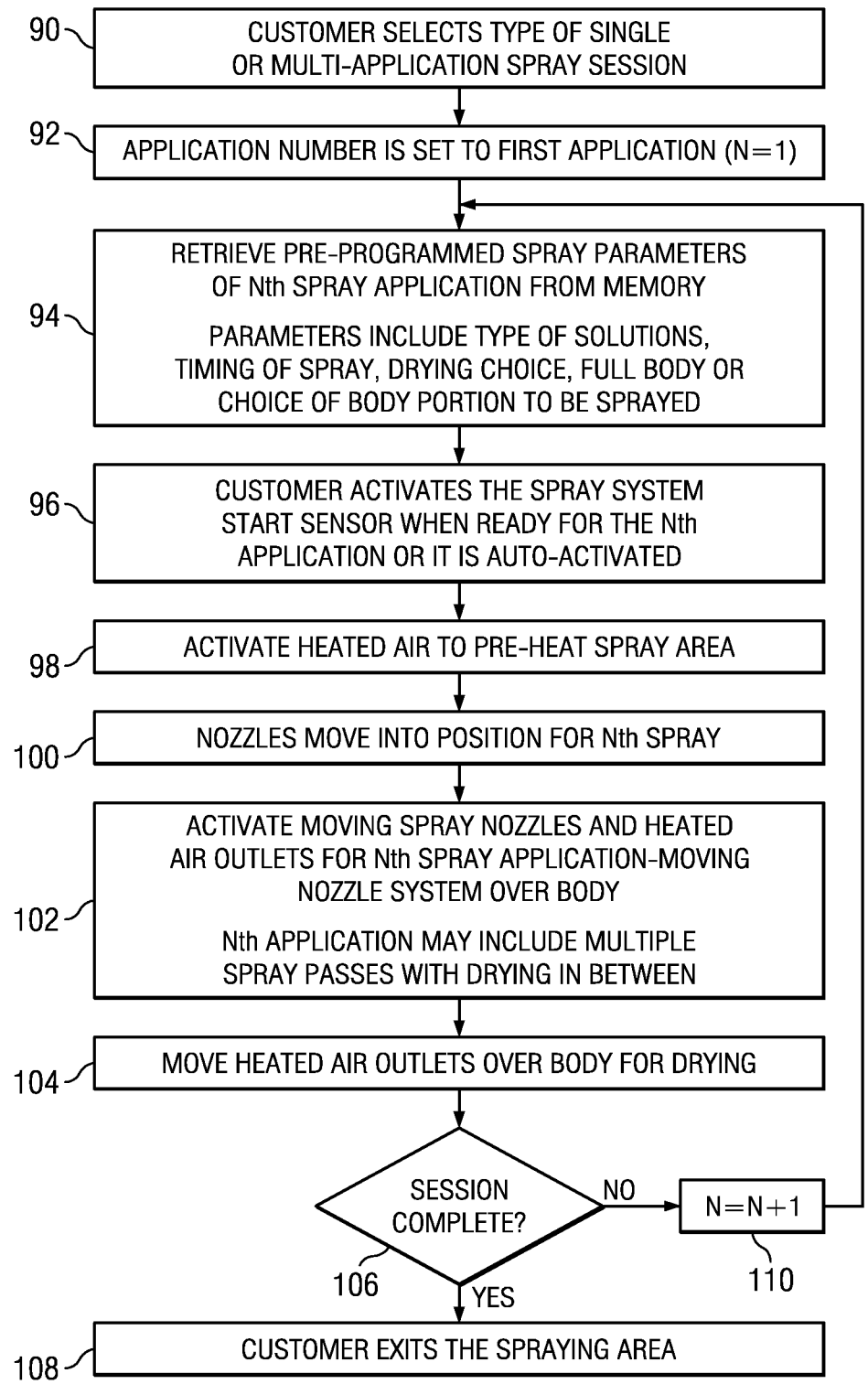
FIG. 9 illustrates a flow diagram for operation of a spraying system which provides for both spraying and drying.

Reference is now made to FIG. 5 which illustrates a perspective view of an HVLP type of spray nozzle 12 with an attached heated (supplemental) air outlet 22. Although only one air outlet 22 is shown, it will be understood that two or more outlets 22 could be included (see, FIG. 1B). This nozzle 12 may include two air inlets (not shown) on the rear of the nozzle body 70; where one inlet provides air to the supplemental air outlet 22 and the other inlet provides air for atomization and pattern shaping at the spray jet outlet 20 through ports 72. In an alternative embodiment, this type of nozzle 12 may include a single air inlet (see FIG. 6) on the rear of the nozzle body 70; where a portion of the received air is directed to the supplemental air outlet 22 and a portion of the received air is directed to the atomizing and pattern shaping ports 72.

FIG. 6 illustrates a cross sectional view of an HVLP type of spray nozzle (such as the nozzle shown in FIG. 5) with a spool valve 74 to control air flow from a single air inlet 76 on the rear of the nozzle body 70 to the atomizing and pattern shaping ports 72 and the supplemental air outlet 22 on the front of the nozzle. Liquid for spraying is received at liquid inlet 78. The flow between ports 72 and the outlet 22 could be manually proportionally adjusted by a knob coupled to the spool valve. Alternatively, manual or automatic adjustment could be achieved by other types of manual or automatic valves which are commercially available (and actuated under the control of the control system 42).

FIGS. 7A, 7B and 7C show that by rotating the spool valve 74 air can be proportionally directed between the drying air outlet 22 and spray and pattern shaping outlets 72. In this way the nozzle can be controlled (for example using the control system described above) into multiple modes of operation. In a first mode, as shown in FIG. 7A, the spool valve 74 is controlled to be in a position for directing air from the air inlet to the supplemental air outlet 22 (but not the atomizing and pattern shaping ports 72) along path 71. In the first mode, the controller system will turn off the valve (reference 60, FIG. 3) supplying spray liquid to the nozzle through inlet 78. In a second mode, as shown in FIG. 7B, the spool valve 74 is controlled to be in a position for directing air to the atomizing and pattern shaping ports 72 (but not the supplemental air outlet 22) along path 73. In a third mode, as shown in FIG. 7C, the spool valve 74 is controlled to be in a position for directing air to both the atomizing and pattern shaping ports 72 and the supplemental air outlet 22 along paths 71 and 73. In this third mode, because the supplied air is being shared between the atomizing and pattern shaping ports 72 and the supplemental air outlet 22, the flow of liquid to the nozzle must be adjusted in a proportional manner. This is accomplished by having the control system (described above) control the actuation of the liquid flow valve 74. Alternatively, if a pressurized liquid reservoir (tank) is used, the control system can selectively perform a venting action to reduce liquid pressure within the tank in proportion to the reduction of air being supplied to the atomizing and pattern shaping ports 72.

Reference is now made to FIG. 8A which shows a side view of an electrostatic air-atomizing nozzle 12 adapted with heated (supplemental) air outlets 22 for use in the system of FIGS. 1A and 1B. The nozzle 12 includes a first air inlet 80 to receive the higher pressure air required for atomization at the spray jet outlet 20 of the liquid received at the liquid inlet 82. The nozzle 12 further includes a second air inlet 84 to receive lower pressure heated air for delivery to the supplemental air outlet(s) 22. Appropriately configured ducting is provided within the nozzle body 86 to couple the supplemental air inlet 84 to the supplemental air outlets 22 in the nozzle cap 88. FIG. 8B shows a front view of the nozzle of FIG. 5A. The supplemental air outlets 22 for supplying warming/drying air are positioned to surround the jet spray outlet 22. It will be understood that an electrostatic nozzle is shown in FIG. 8A (with electrostatic control voltage applied through signal line 85), but that the nozzle of FIG. 8A could, if desired, omit the included electrostatic charging apparatus and operate instead as a conventional, non-electrostatic, air atomizing nozzle (with supplemental air ports as shown).

Reference is now made to FIG. 9 which illustrates a flow diagram for operation of a spraying system which provides for both spraying and drying. In a first step 90, the customer input is received, wherein that customer input selects a type of session with respect to single or multi-application spraying. Multi-application in this context could refer to multiple spray applications of a single product in a single spray session or the sequential application of multiple (different) products in a single spray session. In a second step 92, the application number counter N is initialized to a first application. In a third step 94, the pre-programmed spray parameters of the Nth spray application are retrieved from memory. In a first pass through the flow diagram, these would be the parameters for the first application. Later passes through the flow diagram would retrieve parameters for other applications (second, third, etc.). The parameters which are retrieved may include: type of solution being sprayed, timing of the spray, type of drying to be implemented, which body parts are to be sprayed (for example, whole body or certain body part or parts less than the whole body). In a fourth step 96, the customer activation of the spray system is received. This can be indicated by the customer activating a sensor or switch. Alternatively, this fourth step 96 contemplates an automatic activation of the system, for example after the expiration of a programmable delay time. In a fifth step 98, the system activates the heated air system which operates to supply the heated air into the spray area (this air perhaps comprising supplemental air to that air used by the nozzle for atomization and/or pattern shaping). Where the supplemental air is heated air, as described herein, this fifth step 98 will pre-heat the spray area with heated air for the comfort of the customer. It will be noted that this fifth step 98 is optional, and furthermore this step 98 can alternatively be performed earlier in time, such as when and in response to customer input at step 90. In a sixth step 100, the spray nozzles are moved into a starting position (for example, based on the body parts to be sprayed parameter retrieved above). In a seventh step 102, the spray nozzles are activated to perform the requested spray application. In combination with having the nozzles spray the liquid selected by the customer along with nozzle movement to cover the target this seventh step may additionally supply air to be mixed with the spray cloud. The air in this step 102 is preferably heated so as to warm the spray cloud for the comfort of the customer. Following completion of the seventh step 102 and the spraying of the customer with the liquid, the eighth step 104 causes the system to activate the heated air system in order to supply the heated air into the spray area with movement (for example, by moving the nozzles) over the body surface of the customer. This action is performed so as to accelerate drying of the customer's skin following application of the spray liquid in the seventh step 102. This heated air serves two purposes: a) it dries the skin quickly after spraying which has been shown to enhance the end result of the spraying; and b) it keeps the customer warm. The seventh and eighth steps 102 and 104 may be sequentially repeated for those applications which require multiple spray passes. In the ninth step 106, the system determines whether the customer's requested spray session has been completed. For example, this ninth step 106 tests whether the total number of applications has been reached. If yes, the session is completed, the system turns off and the customer may exit the spray area (step 108). If no, the tenth step 110 increments the application number counter N and the process returns to the third step 94.

In any of the implementations described herein, the heated air may additionally be ionized using an appropriate ionizing apparatus (reference 120, FIG. 3) in the ducting or associated with the air outlets. The ionization of the air delivered from the air outlets of the system is believed to assist in charging the spray cloud so as to improve coating uniformity and reduce overspray.

The spraying systems described herein may be implemented using a fully or partially enclosing spray booth (FIG. 2). For electrostatic spray systems, the surfaces of the booth (or enclosure) may be electrostatically charged. The spray systems may alternatively be implemented without a booth or other enclosure (for example, installed free-standing, or installed in a room, such as a bath or shower).

With respect to an automatic spraying and drying system for skin coating applications, the system is preferably implemented with a moving spray nozzle. In a preferred implementation, that movement is provided through the gantry and vertical movement of the nozzle in a direction (such as provided in a vertical linear direction along the gantry guide track). Alternatively, or additionally, the movement may be provided by oscillating the spray angle of the nozzle. Such oscillation may be horizontal, in the context of a gantry implementation with a vertical translation, or may be vertical (or vertical and horizontal) in the context of an implementation where the nozzles are fixed in position.

Figure 8A:
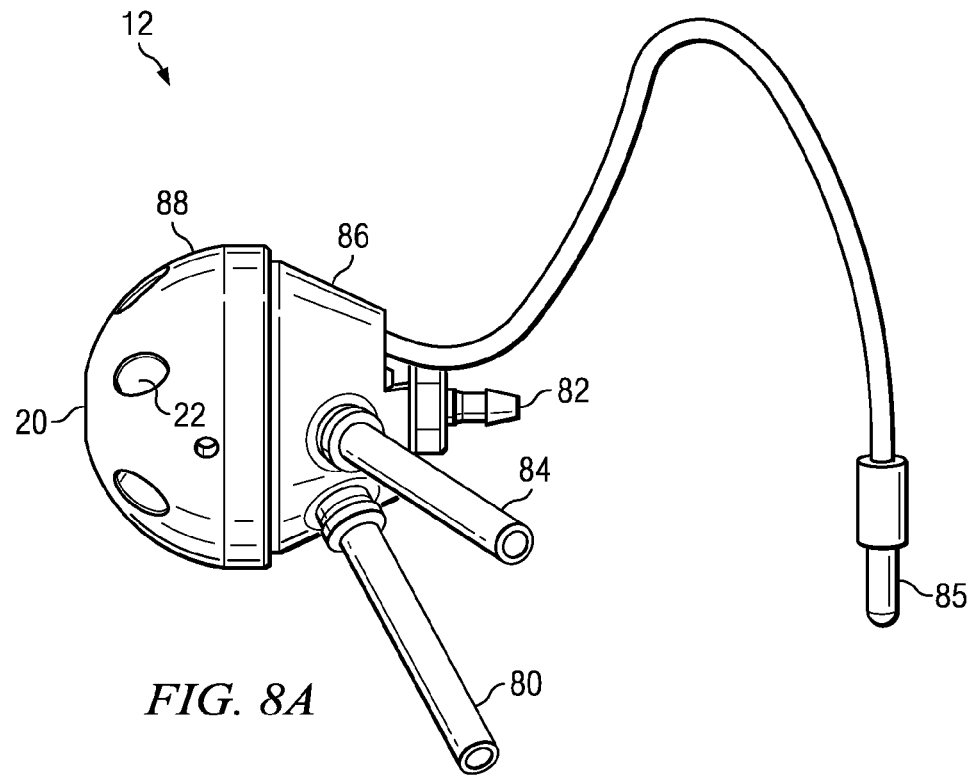
FIGS. 8A and 8B illustrate views of an electrostatic air-atomizing nozzle for use in the spraying system of FIGS. 1A and 1B.
Figure 8B:
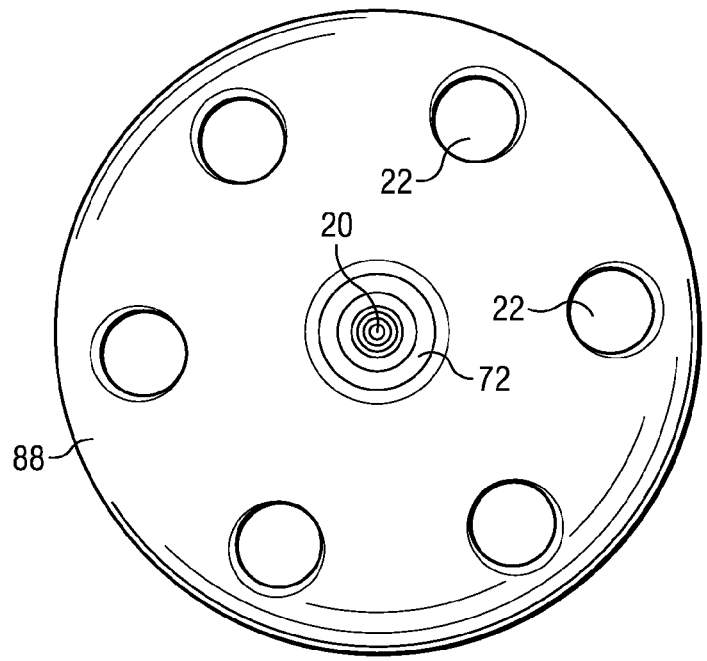

It will be noted that, regardless of nozzle movement implementation, warm air outlets (for example, outlets 22') will be provided and positioned so as to direct air towards the customer target, and preferably move with any movement (translation and/or oscillation) of the moving spray nozzle so that heated air delivery intersects with the spray cloud. In one implementation, one or more point sources of heated air are provided about the spray exit (see, for example, FIGS. 4, 5 and 8B). These point sources are preferably positioned so as to provide heated air that mixes with and warms the spray cloud. Even more preferably, these point sources are positioned at the leading and trailing edges of the spray cloud emitted by the spray nozzle (with respect to a primary direction of nozzle movement). In another implementation, one or more point sources of heated air are provided near the nozzle spray jet outlet (see, for example, outlets 22' in FIG. 1A).

Although FIG. 3 illustrates a single liquid tank, it will be understood that this is exemplary and that the system will more likely include multiple tanks, each containing a distinct liquid for customer selection and skin application. When multiple tanks are provided, the customer can make input selections (for example, through the control panel 18) to design a multi-product spray session. The system will adapt its operation (through preprogrammed parameters and under control of the control system 42) to optimize the spray experience based on the liquid selections made by the customer. Alternatively, the system nozzles may be configured to receive small, single use bottles of spray liquid that can be customer selected for each spray session or application.

The control system 42 which is provided for the system will control the operation of the heated air flow, heat levels, nozzle operation, liquid selection, and nozzle movement in accordance with a programmed sequence of operations. An exemplary sequence of operations comprises: pre-heating of the spray area with heated air; application of a first spray solution (with or without heated air); a drying cycle using heated air application; application of a second spray solution (with or without heated air); a drying cycle using heated air application; application of a third spray solution (with or without heated air); and a final drying cycle using heated air application. Another exemplary sequence of operations comprises: pre-heating of spray are with heated air; first pass application of a first spray solution (with or without heated air); a drying cycle using heated air application; second pass application of the same first spray solution (with or without heated air); a drying cycle using heated air application; first pass application of a second spray solution (with or without heated air); a drying cycle using heated air application; second pass application of the same second spray solution (with or without heated air); and a final drying cycle using heated air application.

Improved results using the apparatus and process described herein, with a trial using DHA (dihydroxyacetone) based sunless tanning compounds, include:

Increased tan color by allowing higher quantities of sprayed active ingredient to be deposited due to a layering process where the spray is applied; the skin is re-dried quickly by the warm air flow before another spray pass over the same target area;

Promotes deeper activity of DHA by drying the top layer of skin completely and possibly by drying inner layers of the stratum corneum skin layer; this results in longer lasting tan color;

Opens skin surface pores to allow for better penetration of tanning compound and skin care ingredients;

Properly controlled heated air dries the skin of any perspiration or other moisture, including the water based spray itself, that may cause an uneven tanning effect and prevent penetration into skin layers;

Prevents dripping or streaking of the sprayed material during the tanning process which can cause an uneven tanning result; and Eliminates the step of drying the skin off with a towel which causes partial removal and disturbance of the evenly deposited layer from the spray application.

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

What is claimed is:

1. A system, comprising:
a support structure;
a spray housing mounted to and movable with respect to the support structure, the spray housing including a spray nozzle including a spray outlet configured to spray a skin treatment liquid from the spray nozzle in a spray stream which creates a spray cloud and a pattern shaping air outlet adjacent the spray outlet and configured to deliver pattern shaping air into said spray stream for shaping a pattern of the spray stream;
an air outlet mounted to and movable with the spray housing and positioned separate from both the spray outlet and pattern shaping outlet of the spray nozzle, wherein the air outlet is adapted to deliver air in an air stream separate from the spray stream and said pattern shaping air;
a heating unit adapted to heat and deliver the air to the air outlet for the air stream; and
a control system adapted to control operation of the spray outlet and pattern shaping air outlet for the spray nozzle and control operation of the air outlet and control movement of the spray housing with respect to the support structure;
wherein the pattern shaped spray stream is sprayed from the spray outlet along a first trajectory and the heated air stream is delivered from the air outlet along a second trajectory; and
wherein the second trajectory is oriented with respect to the first trajectory so as to supply and mix the heated air stream into the spray cloud created from the pattern shaped spray stream.

2. The system of claim 1, wherein the pattern shaping air outlet of the spray nozzle comprises plural air ports configured to deliver heated air as said pattern shaping air.

3. The system of claim 1, further comprising an additional air outlet provided with a fixed position on the support structure to deliver additional heated air separate from the air stream delivered by the moveable air outlet on the spray housing.

4. The system of claim 1, wherein the support structure comprises a gantry including a movable track, and wherein the spray housing is mounted to and movable along the movable track.

5. The system of claim 1, wherein the spray nozzle is adapted to provide for an oscillatory movement of the pattern shaped spray stream.

6. The system of claim 1, wherein the first and second trajectories intersect each other at a location of a target to which the skin treatment liquid is to be applied.

7. The system of claim 1, wherein the second trajectory is oriented towards a leading or trailing edge of said spray cloud created from the pattern shaped spray stream.

8. The system of claim 1, wherein the heated air is used by the spray outlet of the spray nozzle to air atomize the skin treatment liquid.

9. The system of claim 1, wherein the spray nozzle further comprises a warming air inlet and a valve adapted to selectively direct heated air from the warming air inlet between the spray outlet and the air outlet.

10. The system of claim 9, wherein the valve has a controllable position, wherein the controllable position includes: a first position for directing heated air from the warming air inlet solely towards the spray outlet; a second position for directing heated air from the warming air inlet solely towards the air outlet; and a third position for directing heated air from the warming air inlet towards both the spray outlet and air outlet.

11. The system of claim 1, wherein the system imparts an electrostatic charge to the spray stream.

12. The system of claim 1, wherein the air outlet is coupled to the spray nozzle, and wherein the spray nozzle comprises a first air inlet coupled to supply air to the spray outlet for air atomizing the liquid, and a second air inlet coupled to supply heated air to the air outlet.

13. The system of claim 1, wherein the control system is further adapted to control movement of the air stream and pattern shaped spray stream to spray the skin treatment liquid and direct heated air across a target to which the skin treatment liquid is to be applied.

14. The system of claim 1, wherein the control system is further adapted to control the spraying of the skin treatment liquid and directing of heated air towards a target to which the skin treatment liquid is to be applied by alternating a spray of skin treatment liquid with an application of heated air.

15. The system of claim 1, wherein the control system is further adapted to control the spraying of the skin treatment liquid and directing of heated air towards a target to which the skin treatment liquid is to be applied by simultaneously spraying skin treatment liquid and applying heated air.

16. The system of claim 1, wherein the control system is further adapted to control operation of the system in a plurality of modes including:
a first mode wherein the air stream of heated air is delivered from the air outlet simultaneously with spraying of the skin treatment liquid from the spray outlet of the spray nozzle for the purpose of warming the sprayed skin treatment liquid during application of the skin treatment liquid to a target surface; and a second mode wherein the air stream of heated air is delivered from the air outlet alternately with spraying of the skin treatment liquid from the spray outlet of the spray nozzle for the purpose of drying a target surface.

17. The system of claim 16, further comprising a third mode wherein the air stream of heated air is delivered from the lower pressure air outlet prior to spraying of the skin treatment liquid from the higher pressure air outlet of the spray nozzle for the purpose of preparing a target surface to receive the sprayed skin treatment liquid.

18. The system of claim 1, further comprising a booth structure within which the support structure is installed.

19. The system of claim 18, further comprising a venting system installed within the booth structure.

20. A system, comprising:
a support structure;
a spray nozzle assembly mounted to and vertically movable with respect to the support structure, the spray nozzle assembly including a spray jet outlet adapted to generate a spray stream of a skin treatment liquid creating a spray cloud for application to the skin of a human target and one or more pattern shaping air outlets configured to deliver pattern shaping air into said spray stream for shaping a pattern of the spray stream;
an air outlet separate from both the spray jet outlet and the one or more pattern shaping air outlets that is mounted to and vertically movable with the spray nozzle assembly, wherein the air outlet is adapted to deliver heated air in an air stream separate from the spray stream and pattern shaping air which is directed toward the skin of the human target;
a heating unit adapted to heat the air for the air stream that is delivered from the air outlet; and
a control system adapted to control operation of the spray nozzle assembly to generate the pattern shaped spray stream and control operation of the air outlet to generate the air stream, said control system further adapted to control vertical movement of the spray nozzle assembly and air outlet so as to sweep the pattern shaped spray stream and air stream across the human target for application to the skin of the human target of the skin treatment liquid.

21. The system of claim 20, wherein the one or more pattern shaping air outlets of the spray nozzle assembly comprises a plurality of air ports configured to deliver heated air as said pattern shaping air.

22. The system of claim 20, further comprising an additional air outlet provided at a fixed position on the support structure and configured to deliver additional air separate from the pattern shaped air stream delivered by the air outlet and the pattern shaping air.

23. The system of claim 20, wherein the support structure comprises a vertical gantry track, and wherein the spray nozzle assembly is mounted to and vertically movable along the vertical gantry track.

24. The system of claim 20, wherein the spray nozzle assembly is adapted for oscillatory movement of the pattern shaped spray stream.

25. The system of claim 20, wherein the spray stream is sprayed with a first horizontally oriented trajectory and the heated air in the air stream is delivered with a second horizontally oriented trajectory.

26. The system of claim 20 wherein the spray stream is sprayed with a first trajectory and the heated air in the air stream is delivered with a second trajectory, further wherein the second trajectory directs the air stream towards a leading or trailing edge of said spray cloud.

27. The system of claim 20, wherein the heated air is used at an atomizing air outlet of the spray jet outlet to air atomize the skin treatment liquid to form the spray stream.

28. The system of 27, wherein the spray nozzle assembly further comprises a warming air inlet and a valve adapted to selectively direct heated air from the warming air inlet between the atomizing air outlet and the air outlet.

29. The system of claim 28, wherein the valve has a controllable position, wherein the controllable position includes: a first position for directing heated air from the warming air inlet solely towards the atomizing air outlet; a second position for directing heated air from the warming air inlet solely towards the air outlet; and a third position for directing heated air from the warming air inlet towards both the atomizing air outlet and air outlet.

30. The system of claim 20, wherein the system imparts an electrostatic charge to the spray stream.

31. The system of claim 20, wherein the air outlet is coupled to the spray nozzle assembly, and wherein the spray nozzle assembly comprises a first air inlet coupled to supply air to an atomizing air outlet for air atomizing the liquid to form the spray stream, and a second air inlet coupled to supply heated air to the air outlet.

32. The system of claim 20, wherein the control system is further adapted to control vertical movement of the air stream and pattern shaped spray stream to spray the skin treatment liquid and direct heated air across the human target to which the skin treatment liquid is to be applied.

33. The system of claim 20, wherein the control system is further adapted to alternate spraying of the skin treatment liquid and application of heated air.

34. The system of claim 20, wherein the control system is further adapted to simultaneously spray the skin treatment liquid and apply heated air.

35. The system of claim 20, wherein the control system is further adapted to control operation of the system in a plurality of modes including:
a first mode of simultaneously spraying the skin treatment liquid and applying heated air; and
a second mode of alternately spraying of the skin treatment liquid and applying heated air.

36. The system of claim 35, further comprising a third mode of applying heated air prior to spraying the skin treatment liquid.

37. The system of claim 20, further comprising a booth structure within which the support structure is installed.

38. The system of claim 37, further comprising a venting system installed within the booth structure.

39. The system of claim 1, wherein the control system is further adapted to control an amount of heat provided by the heating unit.

40. The system of claim 39, wherein the control system is further adapted to control at least one of an air source and the heating unit providing adjustability of the heated air delivered from the air outlet.

41. The system of claim 20, wherein the control system is further adapted to control an amount of heat provided by the heating unit.

42. The system of claim 41, wherein the control system is further adapted to control at least one of an air source and the heating unit providing adjustability of the heated air delivered from the air outlet.

* * * * *